US009723860B2

(12) United States Patent
Boomsma et al.

(10) Patent No.: US 9,723,860 B2
(45) Date of Patent: Aug. 8, 2017

(54) METHOD FOR IMPROVING ECONOMIC PERFORMANCE IN POULTRY HUSBANDRY

(71) Applicant: PURAC BIOCHEM BV, Gorinchem (NL)

(72) Inventors: Bart Jan Boomsma, Gorinchem (NL); Anne Cazemier, Gorinchem (NL)

(73) Assignee: PURAC BIOCHEM BV, Gorinchem (NL)

( * ) Notice: Subject to any disclaimer, the term of this patent is extended or adjusted under 35 U.S.C. 154(b) by 0 days.

(21) Appl. No.: 14/390,877

(22) PCT Filed: Apr. 3, 2013

(86) PCT No.: PCT/EP2013/056998
§ 371 (c)(1),
(2) Date: Oct. 6, 2014

(87) PCT Pub. No.: WO2013/150058
PCT Pub. Date: Oct. 10, 2013

(65) Prior Publication Data
US 2015/0057345 A1 Feb. 26, 2015

Related U.S. Application Data

(60) Provisional application No. 61/620,471, filed on Apr. 5, 2012.

(30) Foreign Application Priority Data

Apr. 5, 2012 (EP) .................................. 12163374

(51) Int. Cl.
*C07C 59/00* (2006.01)
*A23K 1/18* (2006.01)
(Continued)

(52) U.S. Cl.
CPC .......... *A23K 1/1826* (2013.01); *A23K 20/105* (2016.05); *A23K 50/75* (2016.05); *C07C 69/67* (2013.01)

(58) Field of Classification Search
CPC .... A23K 1/1826; A23K 50/75; A23K 20/105; C07C 69/67
(Continued)

(56) References Cited

U.S. PATENT DOCUMENTS

2005/0019461 A1* 1/2005 Cazemier ............. A23K 1/1826
426/335
2010/0311832 A1* 12/2010 Cazemier ............... A61K 31/23
514/547

FOREIGN PATENT DOCUMENTS

CN 1835686 A 9/2006
EP 2 371 226 A2 10/2011
(Continued)

OTHER PUBLICATIONS

Lensing M et al: "Efficacy of a lactylate on production performance and intestinal health of broilers during a subclinical Clostridium perfringens infection", Nov. 2010, Poultry Science, vol. 89, Nr.11, pp. 2401-2409.*
(Continued)

Primary Examiner — Deborah D Carr
(74) Attorney, Agent, or Firm — Oliff PLC

(57) ABSTRACT

Method for improving the feed efficiency in poultry husbandry wherein poultry is provided with a compound directly upon hatching, the compound being selected from a lactylate in accordance with formula 1, or a Na, K, Ca, Mg, Fe(II), Zn, NH4, or Cu(II) salt thereof, R2-COO—[—CH(CH3)-COO]n-R1          Formula 1 a glycolylate of formula 2, or a Na, K, Ca, Mg, Fe(II), Zn, NH4, or Cu(II) salt thereof.
(Continued)

$$\text{R2-COO—[—CH2-COO]}n\text{-R1} \quad \text{Formula 2:}$$

a lactate ester of formula 3, $$\text{HO—CH(CH3)-COO—R2} \quad \text{Formula 3:}$$

and/or a glycolic acid ester of formula 4, $$\text{HO—CH2-COO—R2} \quad \text{Formula 4:}$$

In the above formulas R1 is selected from H, n stands for an integer with value of 1-10, and R2 stands for C1-C35 alkyl or alkenyl chain, which may be branched or unbranched. The effective compound provided to poultry is dosed level in a first part of their life-span higher than the dose level in other part of their life span.

16 Claims, 1 Drawing Sheet

(51) Int. Cl.
  *C07C 69/67*   (2006.01)
  *A23K 20/105*  (2016.01)
  *A23K 50/75*   (2016.01)

(58) Field of Classification Search
  USPC .......................................................... 554/213
  See application file for complete search history.

(56) References Cited

FOREIGN PATENT DOCUMENTS

| NL | WO 2009092787 A1 * | 7/2009 | ........... A23K 1/1609 |
| WO | WO 2009/092787 A2 | 7/2009 | |

OTHER PUBLICATIONS

Lensing et al., "Efficacy of a Lactylate on Production Performance and Intestinal Health of Broilers During a Subclinical *Clostridium perfringens* Infection," *Poultry Science*, Nov. 2010, vol. 89, No. 11, pp. 2401-2409.

International Search Report issued in International Application No. PCT/EP2013/056998 mailed May 28, 2013.

Written Opinion of the International Searching Authority issued in International Application No. PCT/EP2013/056998 mailed May 28, 2013.

* cited by examiner

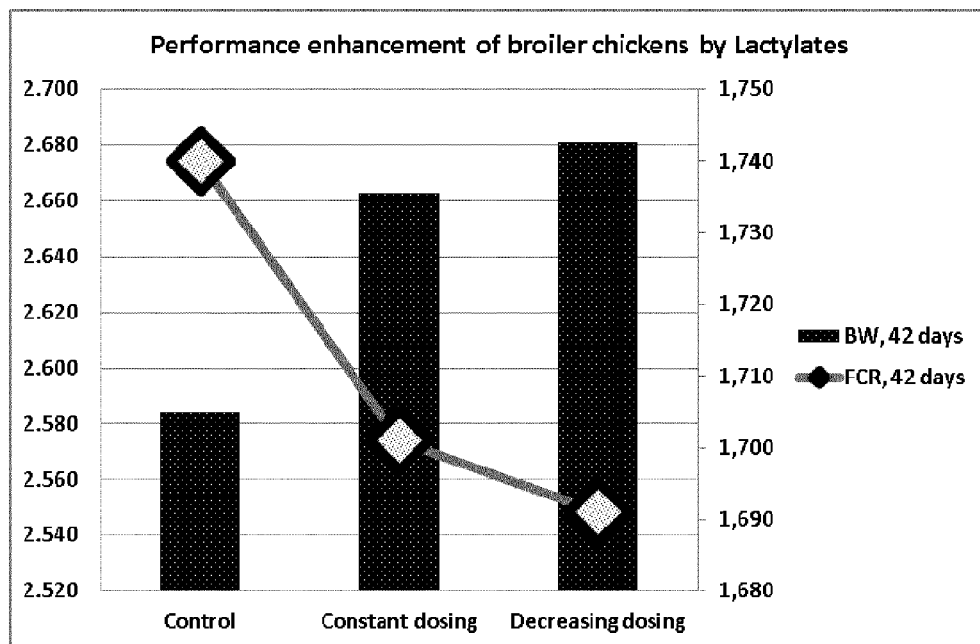

METHOD FOR IMPROVING ECONOMIC PERFORMANCE IN POULTRY HUSBANDRY

The present invention pertains to a method for improving economic performance in poultry husbandry, often determined as feed efficiency. The efficiency at which poultry converts feed into product is an important parameter in poultry husbandry. A first aspect is the efficiency of the conversion of feed into body weight. This may be expressed by way of the feed-to-gain ratio, which is the ratio between the weight of feed provided per unit of time, e.g., per day, and the body weight increase per the same unit of time. This aspect is of importance for poultry which is kept for meat production. For poultry which is kept for eggs, the feed efficiency may be expressed as the feed to egg ratio, which is the ratio between the feed provided per unit of time, e.g., per day, and the egg weight produced per the same unit of time. As an increase in food efficiency is of significant commercial importance, there is therefore always a need for methods to improve feed efficiency, and for animal feed compositions and additives which provide this effect.

It has now been found that the provision to poultry of a specific compound in accordance with a specific dosage regimen results in an improved feed efficiency. In one embodiment, the improvement in feed efficiency is in the form of an improved feed to gain ratio. In another embodiment it is in the form of an improved feed to egg ratio.

In the method according to the invention poultry is provided with an effective compound directly upon hatching, the effective compound being selected from a lactylate in accordance with formula 1, or a Na, K, Ca, Mg, Fe(II), Zn, NH$_4$, or Cu(II) salt thereof,

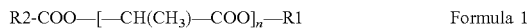
R2-COO—[—CH(CH$_3$)—COO]$_n$—R1    Formula 1 a glycolylate of formula 2, or a Na, K, Ca, Mg, Fe(II), Zn, NH$_4$, or Cu(II) salt thereof.

R2-COO—[—CH$_2$—COO]$_n$—R1    Formula 2:

a lactate ester of formula 3,

HO—CH(CH$_3$)—COO—R2    Formula 3:

and/or a glycolic acid ester of formula 4,

HO—CH$_2$—COO—R2    Formula 4:

wherein in the above formulas R1 is selected from H, n stands for an integer with a value of 1-10, and R2 stands for a C1-C35 alkyl or alkenyl chain which may be branched or unbranched.

While not wishing to be bound by theory, it is believed that the present invention primes the constitution of the animal for optimized growth performance in its development phase.

In the context of the present specification, providing an animal with an effective compound directly upon hatching means that the compound is provided to the animal within 72 hours from hatching. It is preferred that the animal is provided with the effective compound within 48 hours from hatching; provision with 36 hours is more preferred, provision within 24 hours is particularly preferred.

It has been found that the provision of the specified compound in this particular stage of the animal life gives an improved feed efficiency as compared to the situation where this compound is not provided in the starting phase, but only in later parts of the life cycle.

In this context it is noted that WO 2009/092787 describes the provision of compounds of this type in a method for prevention and treatment of infections caused by Gram-positive bacteria in animals, int. al. poultry. As appears from the examples, the compound is only provided to the animals, in this case chickens, starting at day 9.

EP2371226 describes the provision of sodium stearoyl-2-lactylate to animals to improve their fat utilization efficiency. Again, the compound is provided only to animals at a certain age.

The effect of the compound will start with an individual dose. However, it has been found that the effect of the invention will best be obtained if the compound is provided for a longer period of time. However, as long as the compound is provided directly upon hatching, it is not necessary to continue the provision after that period. E.g. provision of the compound to the animal in the so-called grower of finisher phases of its life cycle may not be required. This will be elucidated in more detail below.

Within the meaning of the present specification, the word "poultry" is intended to encompass all domesticated birds kept by humans for the purpose of producing eggs, meat, and/or feathers. Examples of suitable poultry include chicken, turkey, ducks, pheasant, quail, geese, guinea fowls, and ratites. The invention has been found to be particularly suitable for poultry raised for meat production to improve the feed to gain ratio, in particular for broilers, which are chickens raised specifically for meat production. In another embodiment, the invention is applied in raising and keeping poultry raised and kept for egg production, such as laying hens. The use in broiler husbandry is particularly preferred.

It has been found that the provision of the effective compound directly upon hatching allows the use of a lower amount of compound to obtain a certain feed efficiency, e.g., feed to gain ratio or feed to egg ratio, than when the compound is provided only at a later point in time.

The invention also relates to a compound selected from a lactylate in accordance with formula 1, or a Na, K, Ca, Mg, Fe(II), Zn, NH$_4$, or Cu(II) salt thereof,

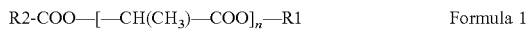
R2-COO—[—CH(CH$_3$)—COO]$_n$—R1    Formula 1 a glycolylate of formula 2, or a Na, K, Ca, Mg, Fe(II), Zn, NH$_4$, or Cu(II) salt thereof

R2-COO—[—CH$_2$—COO]$_n$—R1    Formula 2:

a lactate ester of formula 3,

HO—CH(CH$_3$)—COO—R2    Formula 3:

and/or a glycolic acid ester of formula 4,

HO—CH$_2$—COO—R2    Formula 4:

wherein in the above formulas R1 is selected from H, n stands for an integer with a value of 1-10, and R2 stands for a C1-C35 alkyl or alkenyl chain which may be branched or unbranched for use in improving the feed efficiency in poultry husbandry wherein poultry is provided with a compound directly upon hatching.

In one embodiment, the effective compound is provided to poultry in such a manner that the dosing level provided in a first part of their life-span is higher than the dosing level provided in a further part of their life span. The dosing level is defined as the weight of effective compound provided divided by the weight of the solid feed provided to the animal. It should be noted that even though the dosing level is calculated as the percentage of the weight of the effective compound per the weight of the solid feed, the compound does not have to be present in the feed. As will be discussed in more detail below, the compound may in fact be present in the solid feed itself, but may also be provided in the drinking water or in a separate step.

In one embodiment, the effective compound is provided to poultry in such a manner that the dosing level provided in a first part of their life-span is higher than the dosing level in a second part of their life span, which is higher than the dosing level provided in a third part of their life span.

The compound may be provided in accordance with various dosing regimens. For example, it may be provided at least once during a certain part of an animal's lifespan, at least twice during a certain part of an animal's life span, or more often. The compound may be provided, e.g., at least once a week, or at least twice a week, or at least every three days, or at least every two days, or at least once a day, during a certain phase in the animal's life. If so desired, the compound may be provided with every feed. It may be preferred for the compound to be homogeneously distributed through the feed so that appropriate intake by the animals may be ensured.

In one embodiment, for example, broilers may be provided with the effective compound in accordance with the following regimen:

Prestarter phase: dosing level of 0.03-3 wt. %
Starter phase: dosing level of 0% to 2% wt. %
Grower phase: dosing level of 0% to 1 wt. %
Finisher phase: dosing level of 0% to 1 wt. % wherein the dosing level in the prestarter phase is higher than the dosing level in any one of the starter phase, the grower phase, or the finisher phase.

The dosing level in the starter phase may be the same as the dosing level provided in the grower phase. The dosing level in the starter phase may also be higher than that in the grower phase, but it will in general not be lower. The dosing level in the grower phase may be the same or higher than that in the finisher phase, but it will in general not be lower. In one embodiment, the dosing level in the prestarter phase is higher than the dosing level in the starter phase, which is in turn the same as or higher, preferably higher, than the dosing level in the grower phase, which is in turn the same as or higher, preferably higher, than the dosing level in the finisher phase.

For broilers the prestarter phase will generally range from day 0 to day 5-14, depending on the growth regimen applied. The starter phase will generally range from the end of the prestarter phase to day 14/21, depending on the growth regimen applied. The grower phase will generally range from the end of the starter phase to day 35/56, depending on the growth regimen applied. The finisher phase will generally range from the end of the grower phase to the end of life. The skilled person active in chicken husbandry will be aware of the different phases in a chicken's life cycle, which may be characterised by one or more of different feed composition, different temperature conditions, different light-darkness regimen, and different housing conditions.

For other animals kept for meat production equivalent schedules may be applied, depending on the life cycle of the animal in question.

For animals kept for egg production, in particular laying hens, the following schedule may be applied:

first rearing phase (day 0 to day 14-28): dosing level of 0.03-3 wt. %,
second rearing phase (end of first rearing phase to day 110-150): dosing level of 0-2 wt. %
laying phase (end of second rearing phase-end of life): 0-2 wt. %.

The dosing level in the first rearing phase may be the same as the dosing level provided in the second rearing phase. The dosing level in the first rearing phase may also be higher than that in the second rearing phase, but it will in general not be lower. The dosing level in the second rearing phase may be the same or higher than that in the laying phase, but it will in general not be lower.

In one embodiment, the dosing level in de first rearing phase is higher than the dosing level in the laying phase. In one embodiment the dosing level in the first rearing phase is in the range of 0.25-1.5 wt. %, while the dosing level in the laying phase is in the range of 0.1-1 wt. %, the latter preferably being lower than the former. In one embodiment, the dosing level in the first rearing phase the same as or higher, preferably higher than the dosing level in the second rearing phase, which is in turn the same as or higher, preferably higher, than the dosing level in the laying phase.

As indicated above, the effective compound is selected from a lactylate in accordance with formula 1, or a Na, K, Ca, Mg, Fe(II), Zn, NH$_4$, or Cu(II) salt thereof,

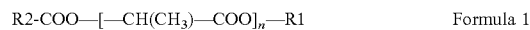

R2-COO—[—CH(CH$_3$)—COO]$_n$—R1       Formula 1 a glycolylate of formula 2, or a Na, K, Ca, Mg, Fe(II), Zn, NH$_4$, or Cu(II) salt thereof.

R2-COO—[—CH$_2$—COO]$_n$—R1       Formula 2:

a lactate ester of formula 3,

HO—CH(CH$_3$)—COO—R2       Formula 3:

and/or a glycolic acid ester of formula 4,

HO—CH$_2$—COO—R2       Formula 4:

wherein in the above formulas R1 is selected from H, n stands for an integer with a value of 1-10, and R2 stands for a C1-C35 alkyl or alkenyl chain which may be branched or unbranched.

The use of a lactylate of formula 1 or a salt thereof has been found to be preferred.

In a preferred embodiment of the present invention, R2 is an alkyl or alkenyl chain with 6-20 carbon atoms. More in particular, R2 is an alkyl or alkenyl chain with 6-18 carbon atoms. In this embodiment, suitable substituents include groups with 6 carbon atoms (capronic), 8 carbon atoms (caprylic) 10 carbon atoms (capric acid), 12 carbon atoms (lauryl), 14 carbon atoms (myristyl), 16 carbon atoms (cetyl, palmityl), 18 carbon atoms (stearyl). Mixtures of two or more compounds may also be used. Where a salt is used, the use of a Na, K, Ca, or Mg salt may be particularly preferred.

The value for n is preferably in the range of 1-5. More in particular n has a value of 1, 2, or 3.

The use of lauroyl lactylate, myristolyl lactylate, and their sodium salts is particularly preferred. In one embodiment, a mixture is used comprising 5-95 wt. % of lauroyl lactylate and 95-5 wt. % of myristoyl lactylate, or the sodium salt(s) of these compounds are used, more in particular, a mixture is used comprising 25-75 wt. %, more in particular 40-60 wt. % of lauroyl lactylate, and 75-25 wt. %, more in particular 40-60 wt. % of myristoyl lactylate, or the sodium salt(s) of these compounds.

The effective compound may be administered to poultry as a component of a conventional feed composition for the animal at issue. In the context of this invention the term "animal nutrition" includes solid feed and liquid feed, such as drinking water. Thus, the composition may be administered to an animal as a solid or liquid component of a conventional feed composition or in their drinking water. The composition may also be administered to the animal in a separate step, independent from the provision of a conventional animal feed composition.

A conventional animal feed composition may comprise wheat, starch, meat and bone meal, maize, sunflower meal, corn, cereals, barley, soybean meal, tapioca, citrus pulp, legumes, beet pulp, and oils and fats of animal or vegetable origin, and so on.

In one embodiment of the invention, the effective compound, in particular the lactylate or salt thereof, is attached to a support. This provides a convenient way to obtain the effective composition in solid powdered form. Suitable supports are selected from vegetable fiber material, vegetable carbohydrates such as cellulose, and mineral supports such as silica, starch, gypsum, and lime. In another embodiment, the effective compound is added in a mixture with an oil, e.g., a corn oil, soybean oil, olive oil. The effective compound may also be in the form of a tablet or other shaped body known for provision of pharmaceutical components to animals.

The amount of effective compound, in particular lactylate, administered to the animal is such that it is effective to treat or prevent intestinal infections caused by Gram-positive bacteria in the animal to which the compound is administered. Such an amount is suitably in the range from 0.0001-5% based on the total weight of each feed fed to the animal. In a preferred embodiment, the amount may be in the range of 0.001 to 2%, based on the total weight of each feed fed to the animal. Accordingly, in one embodiment of the present invention the amount may be in the range of 0.001 to 1 wt. %, more in particular 0.001 to 0.5 wt. %, based on the total weight of each feed fed to the animal. It is within the scope of the skilled person to determine the amount necessary.

The invention also relates to the effective compound as defined here above for improving feed efficiency in poultry husbandry wherein poultry is provided with the compound directly upon hatching.

The invention furthermore relates to the use of an effective compound as defined here above for the preparation of a composition for improving feed efficiency in poultry husbandry wherein poultry is provided with the compound directly upon hatching.

The present invention is elucidated by the following examples, without being limited thereto or thereby.

LEGEND TO FIGURE

FIG. 1: 42 Day performance, visualized. Bars indicate Body Weight (BW) at day 42, scale on left axis. Diamonds indicate Feed-to-Gain ratio (FCR), scale on right axis.

EXAMPLE 1

Efficacy of 0.2% of a Lactylate Mixture of Lauric and Myristic Lactylates on the Economic Performance of Broiler Chickens Broilers were reared on a diet containing 0.2% of a mixture of lauric and myristic lactylates (test diets) or a filler consisting of diatomaceous earth (control diet). The birds fed with the test diet including the lactylates received the lactylates from the first feed onwards.

At day 42, the economic performance of the broilers was evaluated using the body weight, body weight gain, feed consumption and feed-to-gain ratio. Table 1 shows that the economic performance of the broilers fed with lactylates was improved over that of the control group.

TABLE 1

42 day performance of broilers provided with lactylate as feed substituent as compared to control broilers.

| Group | Control | 0.2% Lactylates |
|---|---|---|
| Body weight | 2.751 g | 2.881 g |
| Body weight gain | 2.679 g | 2.825 g |
| Feed Consumption | 4.516 g | 4.512 g |
| Feed-to-Gain ratio | 1.688 g/g | 1.597 g/g |

EXAMPLE 2

Efficacy of Decreasing Levels of a Lactylate Mixture of Lauric and Myristic Lactylates on the Economic Performance of Broiler Chickens Broilers were reared on a diet containing either decreasing levels of a mixture of lauric and myristic lactylates (lactylate test diet), or an effective dose of diclazuril (coccidiostat diet), or a filler consisting of corn starch and kaolin. The birds fed the test diet including the lactylates received the lactylates from the first feed onwards. For the first 10 days, the dosing level of lactylates was 0.4%. From day 11 onwards, the dosing level was reduced to 0.3%.

At day 20, the economic performance of the broilers was evaluated using the body weight, body weight gain, feed consumption and feed-to-gain ratio. Table 2 shows the economic performance of the broilers fed with lactylates was improved over that of the control group. The data show that the lactylate performance enhancement was independent from coccidiosis related illness, as the coccidiostat did not improve performance.

TABLE 2

20 day performance of broilers provided with a decreasing amount of lactylate as feed substituent as compared to control broilers

| Group | Control | Coccidiostat | Lactylates |
|---|---|---|---|
| Body weight | 854 g | 850 g | 893 g |
| Body weight gain | 808 g | 804 g | 847 g |
| Feed Consumption | 1124 g | 1115 g | 1138 g |
| Feed-to-Gain ratio | 1.392 g/g | 1.388 g/g | 1.347 g/g |

EXAMPLE 3

Efficacy of Decreasing Levels of a Lactylate Mixture of Lauric and Myristic Lactylates on the Economic Performance of Broiler Chickens Over a Whole Production Period of 42 Days Broilers were reared on a diet containing either a constant level of a mixture of lauric and myristic lactylates (constant dosing), or a decreasing dose of lauric and myristic lactylates (decreasing dosing) or no additive (control diet). The birds fed the constant dosing diet including the lactylates received the lactylates from the first feed onwards at a level of 0.2%. The birds fed the decreasing dosing diet received the lactylates at a level on 0.3% for the first 10 days. From day 11 until day 20, the dosing level was reduced to 0.2%. From day 21 until slaughter at day 42, the dosing level was reduced to 0.1%. Since daily feed consumption in later stages of broiler life is much greater than in early stages, the decreasing dosing results in a lowering of the overall dosing per broiler.

At day 42, the economic performance of the broilers was evaluated using the body weight, average daily body weight gain, average daily feed intake and feed-to-gain ratio. Table 3 shows the economic performance of both the broilers fed the constant dosing and decreasing dose was improved over that of the control group. The data show that the lactylate performance enhancement was of equal magnitude with the decreasing dosing regimen, as it was with the constant dosing regimen. The decreased amount of lactylate dosed to each animal make the decreasing dosing regimen more economical.

TABLE 3

42 day performance of broilers provided with a decreasing amount of lactylate as feed substituent, broilers provided with a constant amount of lactylate as feed constituent, and control broilers

| Group | Control | Constant dosing | Decreasing dosing |
|---|---|---|---|
| Body weight | 2756 g | 2759 g | 2763 g |
| Average daily weight gain | 64.6 g | 64.7 g | 64.8 g |
| Average daily feed intake | 116.3 g | 114.3 g | 114.9 g |
| Feed-to-Gain ratio | 1.803 g/g | 1.765 g/g | 1.766 g/g |

EXAMPLE 4

Efficacy of Delayed Dosing of a Lactylate Mixture of Lauric and Myristic Lactylates on the Economic Performance of Broiler Chickens Over a Whole Production Period of 42 Days, Repeated Broilers were reared for 42 days at the same facility as in example 3. They were dosed lactylates in a scheme identical to example 3. Table 4 and FIG. 1 show the economic performance of both the broilers fed the constant dosing and decreasing dose was again improved over that of the control group. The data show that the Lactylate performance enhancement was again of equal magnitude with the decreasing dosing regimen, as it was with the constant dosing regimen. Table 4 also shows that the overall dosing of lactylates was lower in the group fed the decreasing dosing scheme, than in the groups fed the constant dosing scheme.

TABLE 4

42 day performance, plus overall lactylates dosing. Values in same rows with no common superscript are significantly different (P < 0.05)

| Group | Control | Constant dosing | Decreasing dosing |
|---|---|---|---|
| Body weight | 2584[b] g | 2663[a] g | 2681[a] g |
| Average daily weight gain | 60.5[b] g | 62.3[a] g | 62.8[a] g |
| Average daily feed intake | 109.1 g | 111.9 g | 113.3 g |
| Feed-to-Gain ratio | 1.740 g/g | 1.701 g/g | 1.691 g/g |

TABLE 4-continued 42 day performance, plus overall lactylates dosing. Values in same rows with no common superscript are significantly different (P < 0.05)

| Group | Control | Constant dosing | Decreasing dosing |
|---|---|---|---|
| Overall Lactylate dosing | 0 g | 8.69 g | 5.67 g |

The invention claimed is:

1. A method for improving the feed efficiency in poultry husbandry,
wherein poultry is provided with an effective compound directly upon hatching, and
wherein the effective compound is provided to poultry in such a manner that a dosing level provided in a first part of their life-span is higher than a dosing level provided in a later part of their life span, the effective compound being at least one selected from the group consisting of:
a lactylate in accordance with formula 1, or a Na, K, Ca, Mg, Fe(II), Zn, NH$_4$, or Cu(II) salt thereof, R2-COO—[—CH(CH$_3$)—COO]$_n$—R1    Formula 1 a glycolylate of formula 2, or a Na, K, Ca, Mg, Fe(II), Zn, NH$_4$, or Cu(II) salt thereof R2-COO—[—CH$_2$—COO]$_n$—R1    Formula 2:

a lactate ester of formula 3,

HO—CH(CH$_3$)—COO—R2    Formula 3:

and a glycolic acid ester of formula 4,

HO—CH$_2$—COO—R2    Formula 4:

wherein in the above formulas R1 is selected from H, n stands for an integer with a value of 1-10, and R2 stands for a C1-C35 alkyl or alkenyl chain which may be branched or unbranched.

2. The method according to claim 1, wherein the compound is provided to poultry kept for meat production.

3. The method according to claim 1, wherein the compound is provided to poultry kept for egg production.

4. The method according to claim 1, wherein the compound is provided to poultry in such a manner that the dosing level provided in a first part of their life-span is higher than the dosing level in a second part of their life span, which is higher than the dosing level provided in a third part of their life span.

5. The method according to claim 1, wherein broilers are provided with the compound in accordance with the following regimen:
Prestarter phase: dosing level of 0.03-3 wt. %
Starter phase: dosing level of 0% to 2 wt. %
Grower phase: dosing level of 0% to 1 wt. %
Finisher phase: dosing level of 0% to 1 wt. %
wherein the dosing level in the prestarter phase is higher than the dosing level in any one of the starter phase, the grower phase, or the finisher phase.

6. The method according to claim 1, wherein laying hens are provided with the compound in accordance with the following regimen:
First rearing phase 0.03-3 wt. %
Second rearing phase 0-2 wt. %
Laying phase 0-2 wt. %
wherein the dosing level in the first rearing phase is higher than the dosing level in the second rearing phase or the laying phase.

7. The method according to claim 1, wherein the compound is a lactylate of formula 1 or a salt thereof for use in improving the feed efficiency in poultry husbandry.

8. The method according to claim 1, wherein the poultry is provided with one or more compounds wherein R2 is an alkyl or alkenyl chain with 6-20 carbon atoms, more in particular 6-18 carbon atoms for use in improving the feed efficiency in poultry husbandry.

9. The method according to claim 1, wherein the poultry is provided with one or more effective compounds selected from lactylates in accordance with Formula 1 in which R2 is an alkyl or alkenyl chain with 6-18 carbon atoms.

10. The method according to claim 9, wherein n in Formula 1 is from 1 to 5.

11. The method according to claim 9, wherein n in Formula 1 is 1, 2 or 3.

12. The method according to claim 9, wherein the poultry is provided with at least one selected from the group consisting of lauroyl lactylate or the sodium salt thereof, and myristoyl lactylate or the sodium salt thereof.

13. The method according to claim 1, wherein the effective compound is provided as a solid or liquid component of a conventional feed composition.

14. The method according to claim 1, wherein the effective compound is attached to a support.

15. The method according to claim 1, wherein the effective compound is provided in a mixture with an oil.

16. The method according to claim 1, wherein the compound is a lactylate of Formula 1 and wherein R2 is an alkyl or alkenyl chain with 12 or 14 carbon atoms.

\* \* \* \* \*